(12) United States Patent
Maly, Jr. et al.

(10) Patent No.: US 11,841,262 B2
(45) Date of Patent: Dec. 12, 2023

(54) METHOD AND SYSTEM OF MONITORING A METER SET USING A SENSOR

(71) Applicant: ROMET LIMITED, Mississauga (CA)

(72) Inventors: Frederick Joseph Maly, Jr., Oakville, MO (US); Mohammadreza Soudmand-Asli, Toronto (CA)

(73) Assignee: ROMET LIMITED, Mississauga (CA)

( * ) Notice: Subject to any disclaimer, the term of this patent is extended or adjusted under 35 U.S.C. 154(b) by 0 days.

(21) Appl. No.: 17/357,460

(22) Filed: Jun. 24, 2021

(65) Prior Publication Data

US 2021/0404858 A1     Dec. 30, 2021

Related U.S. Application Data

(60) Provisional application No. 63/044,207, filed on Jun. 25, 2020.

(51) Int. Cl.
*G01F 25/10*     (2022.01)
*G01F 15/061*    (2022.01)
(Continued)

(52) U.S. Cl.
CPC ............ *G01F 25/10* (2022.01); *G01F 15/061* (2013.01); *G01M 3/26* (2013.01); *G01N 21/31* (2013.01); *G01N 33/28* (2013.01)

(58) Field of Classification Search
CPC ........ G01F 25/10; G01F 15/061; G01F 25/15; G01M 3/26; G01M 3/243; G01N 21/31; G01N 33/28; F17D 5/06
See application file for complete search history.

(56) References Cited

U.S. PATENT DOCUMENTS 10,341,167 B2    7/2019  Arunachalam et al.
2005/0279169 A1  12/2005 Lander
(Continued)

FOREIGN PATENT DOCUMENTS

JP    2008-268091 A   11/2008
WO    2013066316 A1    5/2013

OTHER PUBLICATIONS

Extended European Search Report dated Dec. 16, 2021, 8 Pages, for Corresponding European Patent Application No. 21180809.
(Continued)

*Primary Examiner* — Alexander A Mercado
*Assistant Examiner* — John M Royston

(57) ABSTRACT

By implementing a monitoring system to a fluid meter set, the meter set can be monitored for abnormalities including fluid leaks or other system failures as well as gas blend or gas density. A monitoring system that uses sensors such as vibration sensors can detect fluid leaks or other system failures based on abnormal conditions such as vibrations of the meter set. Sensors may be positioned at various locations along the meter set where leakage of fluids or other system failures may be possible. Sensory information detected by sensors are communicated to processing or control unit which can trigger an alarm signaling unit alerting of a potential fluid leak. Such a system of monitoring the integrity of a fluid meter set can help to quickly identify and respond to a fluid leak without necessarily relying on visual or olfactory cues associated with the fluid being leaked.

21 Claims, 10 Drawing Sheets

(51) Int. Cl.
*G01M 3/26* (2006.01)
*G01N 21/31* (2006.01)
*G01N 33/28* (2006.01)

(56) References Cited

U.S. PATENT DOCUMENTS

| | | | |
|---|---|---|---|
| 2006/0174707 A1* | 8/2006 | Zhang | G01N 29/222 |
| | | | 700/282 |
| 2008/0035202 A1* | 2/2008 | Lee | G01F 25/17 |
| | | | 73/861.61 |
| 2012/0007743 A1* | 1/2012 | Solomon | G01M 3/2807 |
| | | | 702/51 |
| 2019/0027013 A1* | 1/2019 | Sale | G08B 21/182 |

OTHER PUBLICATIONS

International Search Report dated Sep. 20, 2021, 3 Pages, for Corresponding International PCT Patent Application No. PCT/CA2021/050865.
Written Opinion dated Sep. 20, 2021, 6 Pages, for Corresponding International PCT Patent Application No. PCT/CA2021/050865.

* cited by examiner

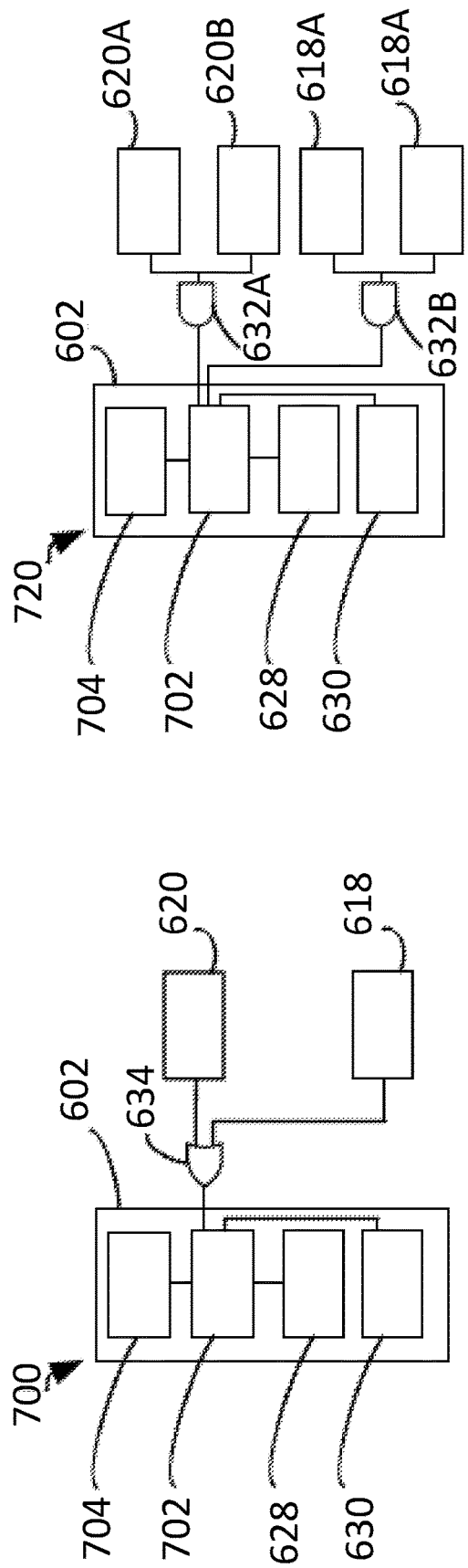
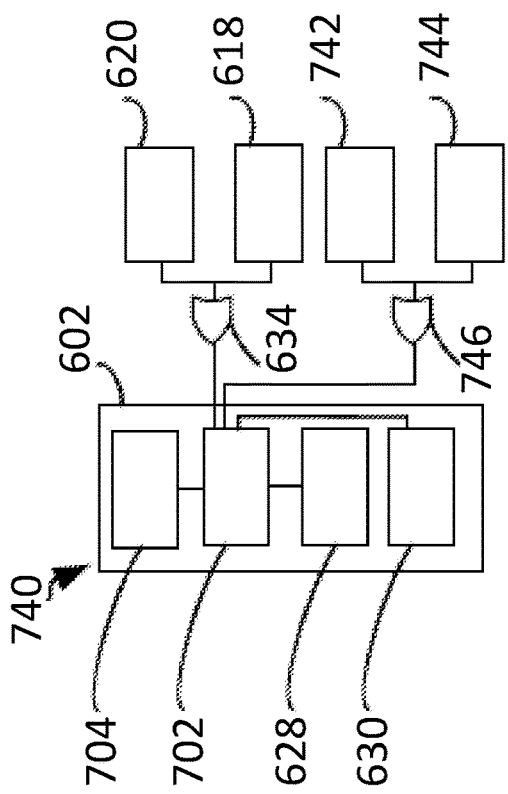
Fig. 7A
Fig. 7B
Fig. 7C

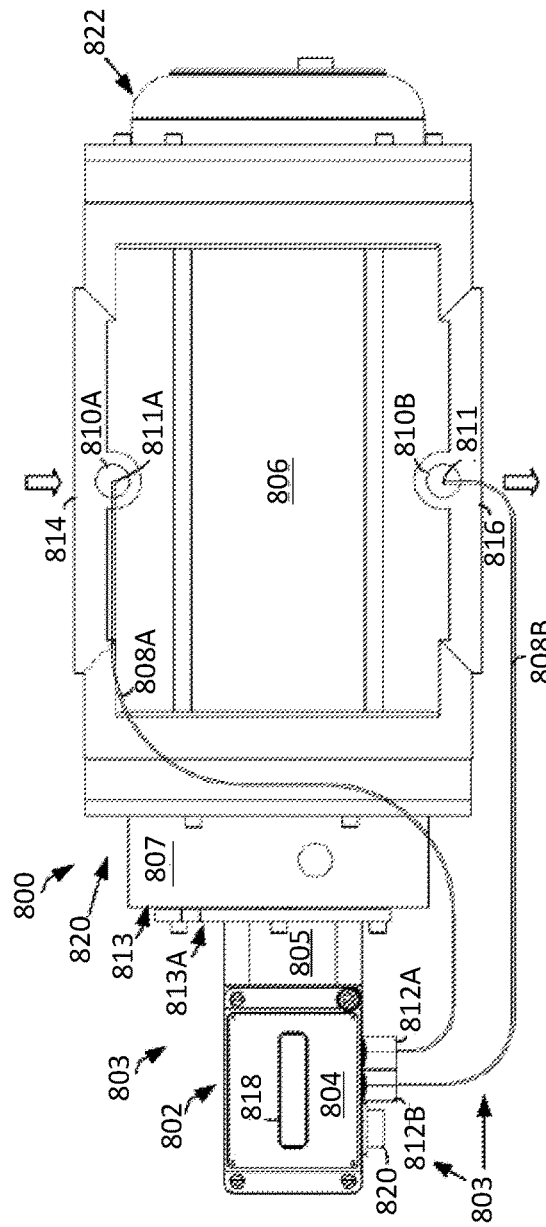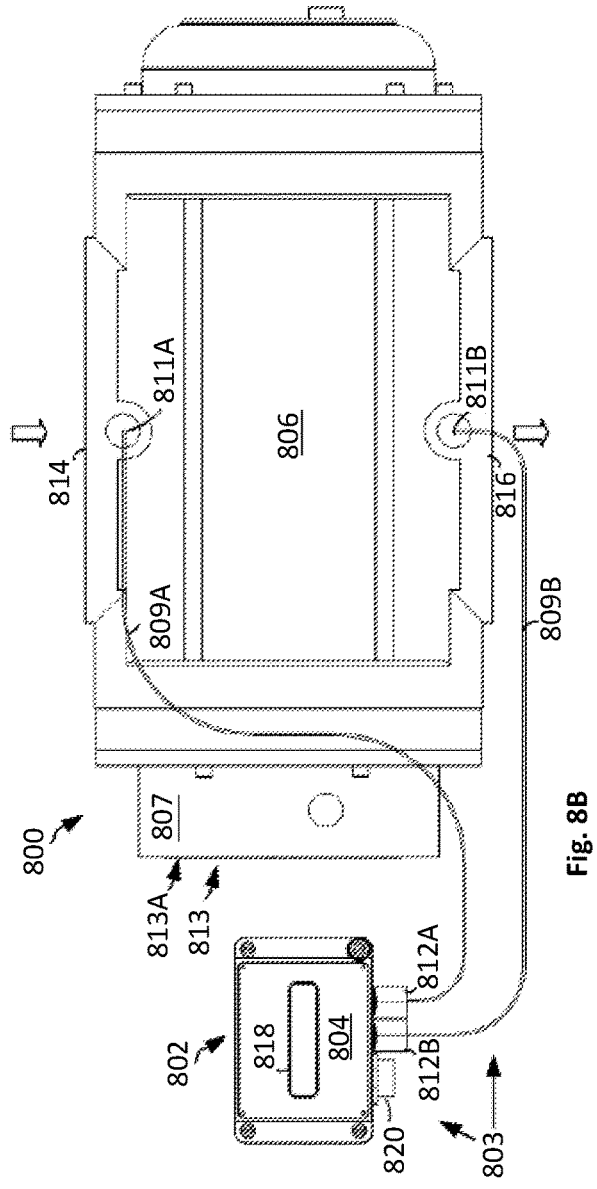
Fig. 8A
Fig. 8B

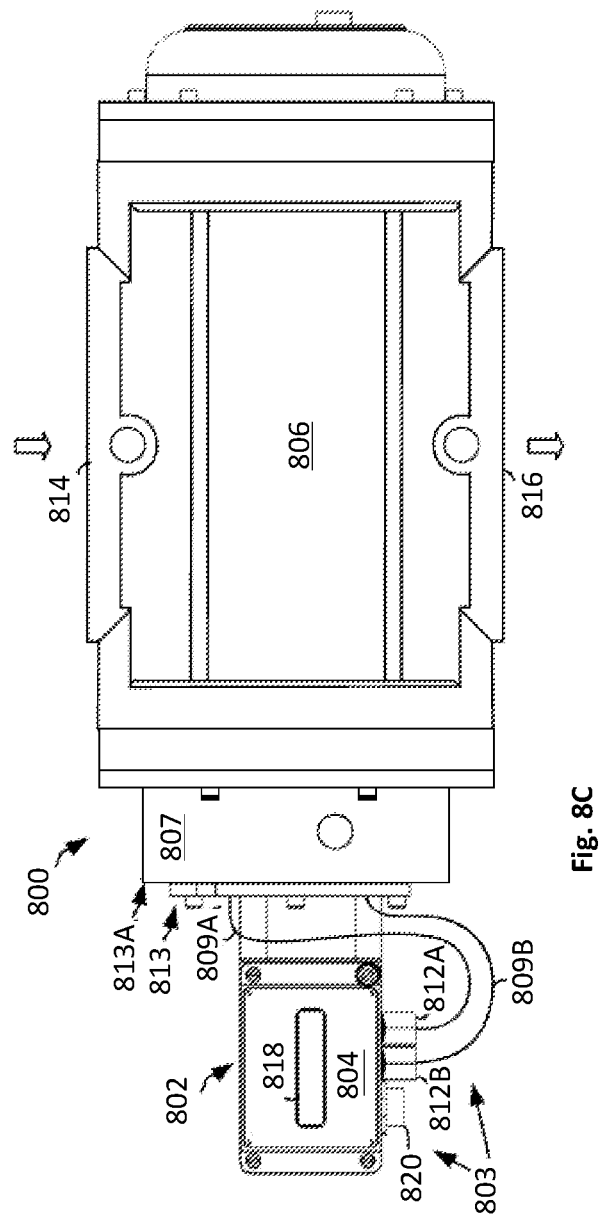

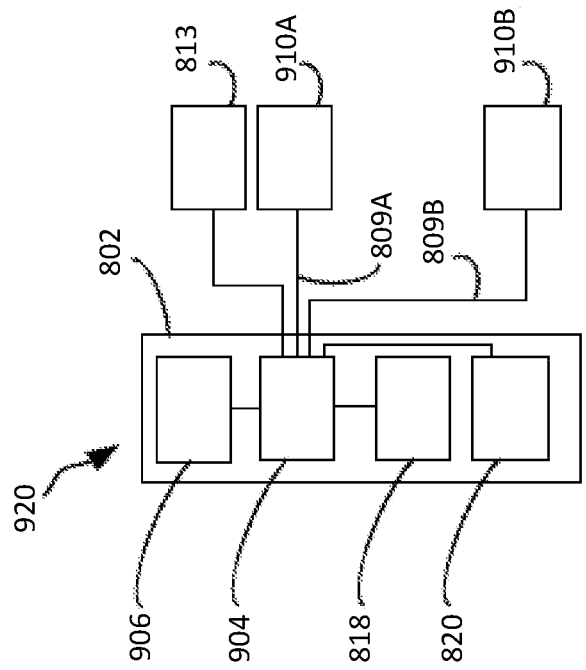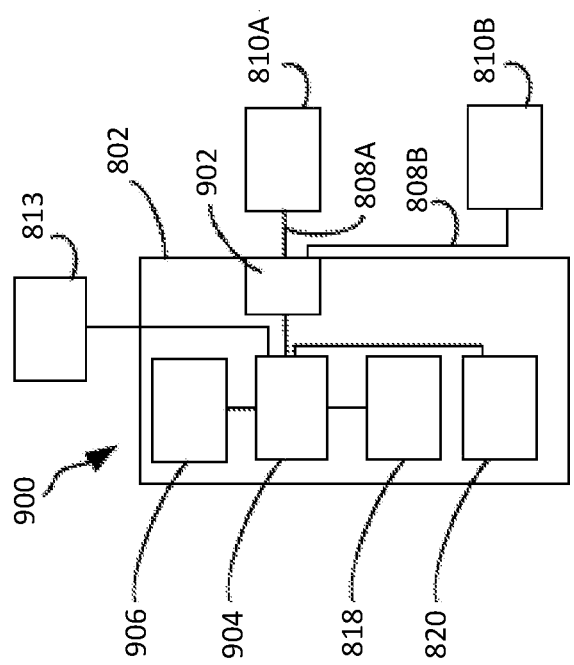

METHOD AND SYSTEM OF MONITORING A METER SET USING A SENSOR

CROSS-REFERENCE

This application claims the benefit of prior U.S. Provisional Application No. 63/044,207 filed Jun. 25, 2020, the respective entire disclosure of which is incorporated by reference herein.

FIELD

The present disclosure relates to monitoring metering systems which measure the distribution of a fluid such as natural gas or mixed gas (e.g. natural gas and hydrogen, sometimes referenced as blended gas), to meter sets for such systems and to monitoring a health of such metering systems. The present disclosure further relates to a monitoring system using one or more vibration sensors to detect abnormal vibrations of the meter set as an indicator of a potential gas leak.

BACKGROUND

Metering systems are widely used to distribute and measure the distribution of fluids such as within a factory, plant, mill or other industrial or non-industrial environment, which environment is not limited to an indoor environment. One type of metering system relates to the distribution of natural gas. Other gases may also be distributed using a metering system, such as mixed gas comprising natural gas and hydrogen. Other gases may be used to prepare a mixed gas. Other fluids, which may be a liquid such as water, may be distributed using a metering system. Common to many metering systems is the use of at least one meter set to measure (and/or regulate) a flow of the respective fluid. Such meter sets are often located remotely about the environment, coupled to piping of the distribution system. Some are difficult to access on a periodic bases for local monitoring of performance or health issues that may affect performance of the meter set, for example, the distribution system more broadly.

Meter sets have various component parts including a rotary meter, turbine meter, ultrasonic meter, diaphragm meter, (natural gas) regulators, control valves, relief valves, electronic instrumentation, pipe fittings and piping. The installation and fitting of these various components creates the opportunity for a meter set to release a respective fluid, (e.g. natural gas) into the atmosphere.

Although many types of gas leaks can be detected by the smell of an odorous chemical added to the gas mixture, such a method of detection relies on a bystander to be in the vicinity of the leak and his/her olfactory senses. Moreover, it requires the bystander to recognize and associate the smell with the gas. Some fluids, like water, are not necessarily detectible through smell. Delayed reporting of a fluid leak is likely to contribute to the continued release of the fluid into the atmosphere. Given the highly flammable nature of many gases, particularly natural gas, this poses an increased risk to life, property and public safety in such distribution systems.

SUMMARY

In accordance with embodiments, a fluid monitoring system that remotely monitors, detects and alerts health or other performance issues provides a more reliable and efficient method of detecting abnormalities including an unexpected (natural gas) leak in a distribution system and/or a meter set. By way of example but without limitation, vibration sensors may be utilized to detect vibrations, pressure sensors may be utilized to detect pressure, and oil condition sensors may be utilized to detect oil condition parameters, such as in a meter set. Any of these and other detected health related signals may be monitored for abnormal changes and alerts raised accordingly.

In accordance with embodiments, in a gas context, there is provided a gas meter set monitoring system and a gas meter set having a gas meter set monitoring system. A gas meter set monitoring system using vibration sensors senses a condition of vibration in the gas meter set or associated elements of the distribution system and the condition may relate to a gas leak. In accordance with embodiments, vibration monitoring detects changes in gas composition, for example, a change in a mixed gas ratio such as a blend of natural gas (methane) and hydrogen.

In accordance with embodiments, a gas meter set monitoring system comprises: at least one vibration sensing unit positioned at a location of a gas meter set to be monitored to provide at least one vibration signal responsive to the operation of the gas meter set; one or more alarm signaling units; and a main control unit configured for coupling to each of the at least one vibration sensing unit and the one or more alarm signaling units. The main control unit is configured to: detect a condition of vibration at the at least one location using the at least one vibration signal; and control at least one of the one or more alarm signaling units to provide an alarm in response to the condition of vibration.

The one or more alarm signaling units may be located locally or in a remote location relative to the at least one vibration sensing unit.

The at least one vibration signal and the corresponding condition of vibration comprises one of an indicator of a gas leak in proximity to the at least one location on a gas meter set; and a change in a composition of the gas.

Each respective vibration sensing unit comprises a communication component to communicate a respective vibration signal to the main control unit. In an embodiment, the vibration signal is communicated without using any communication capabilities of the gas meter set. In an embodiment, the vibration signal is communicated without processing by an electronic volume controller (e.g. a processing unit) of the gas meter set.

A gas meter set may have a gas meter set monitoring system in accordance with the features shown and described.

There is also provided a method of detecting and responding to a detected gas leak from a gas meter set. The method of detection comprises: detecting a condition of vibration at a gas meter set to be monitored using at least one vibration signal received from at least one vibration sensing unit positioned at a location of the gas meter set to be monitored; and controlling at least one of one or more alarm signaling units to provide an alarm in response to the condition of vibration.

The reference vibration signal may be a vibration signal corresponding to the normal operation of the gas meter set in which case a gas leak is determined based on the at least one vibration signal exceeding a threshold level as compared to the reference vibration signal. Alternatively, the reference vibration signal may be a vibration signal corresponding to a confirmed gas leak in which case a gas leak is determined based on the at least one vibration signal substantially matching the reference vibration signal.

After a gas leak is detected, responding to the gas leak would involve communicating the condition of vibration to one or more alarm signaling units to provide an alarm in response to the condition of vibration. The alarm then prompts a response to the gas leak.

The response may be a repair of the gas leak located in proximity to the at least one location on the gas meter set and/or an evacuation from the at least one location on the gas meter set.

In an aspect, there is provided a gas meter set monitoring system comprising: at least one vibration sensing unit each positioned at a respective location of a meter set to be monitored to provide at least one vibration sensing unit signal; and a control unit configured to be coupled to the at least one vibration sensing unit and further to one or more alarm signaling units. The control unit is configured to: detect a condition of vibration from the respective location using the at least one vibration sensing unit signal; and communicate to at least one of the one or more alarm signaling units to provide an alarm signal in response to the condition of vibration.

In an embodiment, the at least one vibration sensing unit comprises at least one vibration sensor, at least one processor and a communication component to communicate the vibration sensing unit signal.

In an embodiment, the condition of vibration corresponds to an abnormality at the at least one location.

In an embodiment, the abnormality (i.e. condition of vibration at the at least one location) comprises any one of: a fluid leak in the meter set; a failure of at least one component of the meter set; a vandalism of the meter set; an unauthorized use of the meter set; a tampering of the meter set; and a change in gas blend or gas density.

In an embodiment, the condition of vibration corresponds to a determination of a gas blend or gas density at the at least one location.

In an embodiment, detecting the condition of vibration comprises comparing a respective vibration sensing unit signal from a respective vibration sensing unit to a stored baseline for the respective vibration sensing unit. In an embodiment, the stored baseline for the respective vibration sensing unit comprises a signal representing one of: a normal operation of the meter set; and an abnormal operation of the meter set. In an embodiment, detecting the condition of vibration is responsive to a current gas blend.

In an embodiment, the control unit is configured to detect the condition of vibration using a classifier.

In an embodiment, during operation, the one or more alarm signaling units are located in a remote location relative to the at least one vibration sensing unit.

In an embodiment, the one or more alarm signaling units comprise a dashboard interface to present the alarm signal.

In an embodiment, the alarm signal alerts of a fluid leak located in proximity to the at least one location.

In an embodiment, in respect of a respective meter set, the control unit is further configured to be coupled to one or more respective meter set sensors sensing a working condition of the respective meter set, each of the one or more respective meter set sensors being separate from the at least one vibration sensing unit and the one or more respective meter set sensors providing a working condition signal; and wherein the control unit is further configured to: detect a working condition of the meter set vibration using a working condition signal; and communicate to at least one of the one or more alarm signaling units to provide an alarm signal in response to the working condition. In an embodiment, the one or more respective meter set sensors comprise any of a pressure sensor and a sensor to measure oil condition.

In an embodiment, the system further comprises a messaging middleware component to communicate between: the at least one vibration sensing unit and the control unit; and the control unit and the one or more alarm signaling units.

In an aspect there is provided a meter set comprising: at least one sensing unit positioned at a respective location of the meter set to provide at least one sensing unit signal; and a meter set processing unit configured to be coupled to the at least one sensing unit and further to one or more alarm signaling units. The meter set processing unit is configured to: receive the at least one sensing unit signal from the at least one sensing unit; detect a condition at the respective location using the at least one sensing unit signal; and communicate to at least one of one or more alarm signaling units to provide an alarm signal in response to the condition.

In an embodiment, the at least one sensing unit comprises at least one sensor and at least one processor.

In an embodiment, one of the at least one sensing unit senses vibration.

In an embodiment, the at least one sensing unit comprises a plurality of sensing units and another of the sensing units senses one of flow rate, fluid levels, differential pressure, and oil condition.

In an embodiment, the condition corresponds to an abnormality at the at least one location.

In an embodiment, the condition is any one of: a fluid leak in the meter set; a failure of at least one component of the meter set; a vandalism of the meter set; an unauthorized use of the meter set; a tampering of the meter set; and a change in gas blend at the meter set.

In an embodiment, the condition corresponds to a determination of a gas blend at the meter set.

In an embodiment, detecting the condition comprises one of: comparing a respective sensing unit signal from a respective sensing unit to a stored baseline for the respective sensing unit; and classifying the respective sensing unit signal from the respective sensing unit using a classifier.

In an embodiment, the stored baseline for the respective sensing unit comprises a signal representing one of: a normal operation of the meter set; and an abnormal operation of the meter set.

In an embodiment, detecting the condition comprises comparing the respective sensing unit signal to a stored baseline and wherein the stored baseline is responsive to a current gas blend.

In an embodiment, during operation of the meter set, the one or more alarm signaling units are located in a remote location relative to the at least one sensing unit.

In an embodiment, the alarm signal alerts of a fluid leak located in proximity to the at least one location.

In an aspect, there is provided a computer implemented method comprising: receiving, at a processing unit, at least one sensing unit signal from at least one sensing unit each positioned at a respective location of a meter set; detecting a condition at the at least one location using the at least one sensing unit; and communicating to at least one of one or more alarm signaling units to provide an alarm signal in response to the condition.

In an embodiment, the at least one sensing unit comprises at least one sensor and at least one processor.

In an embodiment, the at least one sensing unit senses any one of flow rate, fluid levels, differential pressure, oil condition and vibration. For example, the at least one sensing unit may comprise a vibration sensing unit to provide a vibration sensing unit signal representing vibration.

In an embodiment, the condition corresponds to an abnormality at the at least one location.

In an embodiment, detecting a condition comprises one of: comparing a respective sensing unit signal from a respective sensing unit to a stored baseline for the respective sensing unit; and classifying using a classifier. In an embodiment, the stored baseline comprises a signal representing one of: a normal operation of the meter set; and an abnormal operation of the meter set. In an embodiment, the control unit is configured to receive the respective sensing unit signal during either the normal operation or the abnormal operation and define the stored baseline. In an embodiment, detecting the condition comprises the comparing of the respective sensing unit signal from the respective sensing unit to the stored baseline for the respective sensing unit and wherein the comparing is responsive to a current gas blend. In an embodiment, the stored baseline is selected in response to the current gas blend.

In an embodiment, during performance, the one or more alarm signaling units are located in a remote location relative to the at least one sensing unit.

In an embodiment, during performance, the one or more alarm signaling units are locally located relative to the at least one sensing unit.

In an embodiment, the one or more alarm signaling units comprise a dashboard interface to present the alarm signal.

In an embodiment, the condition at the at least one location is any one of: a fluid leak in the meter set; a failure of at least one component of the meter set; a vandalism of the meter set; an unauthorized use of the meter set; a tampering of the meter set; and a change to a gas blend.

In an embodiment, the at least one sensing unit signal is an indicator of a fluid leak in proximity to the at least one location.

In an embodiment, the condition corresponds to a fluid leak in proximity to the at least one location.

In an embodiment, the alarm signal alerts of a fluid leak located in proximity to the at least one location.

In an embodiment, the method is performed by a cloud-based processing unit coupled for communication via one or more networks between the at least one sensing unit and the one or more alarm signaling units.

In an aspect there is provided a computer implemented method comprising: receiving, at a processing unit, at least one vibration sensing unit signal from at least one vibration sensing unit each positioned at a respective location of a meter set; detecting a condition at the at least one location using the at least one vibration sensing unit signal; and communicating to at least one of one or more alarm signaling units to provide an alarm signal in response to the condition. In an embodiment, each respective vibration sensing unit comprises a vibration sensor, a processor and a communication component to communicate a respective sensing unit signal; and the meter set comprises a gas meter set. In an embodiment, the condition corresponds to an abnormality at the at least one location, the abnormality comprising any one of: a fluid leak in the meter set; a failure of at least one component of the meter set; a vandalism of the meter set; an unauthorized use of the meter set; a tampering of the meter set; and a change to a gas blend. In an embodiment, detecting a condition comprises one of: comparing a respective sensing unit signal from a respective sensing unit to a stored baseline for the respective sensing unit; and classifying using a classifier. In an embodiment, when detecting the condition comprises the comparing of the respective vibration sensing unit signal from the respective vibration sensing unit to the stored baseline for the respective vibration sensing unit, the comparing is responsive to a current gas blend, such that the stored baseline is selected in response to the current gas blend.

In an aspect there is provided a cloud-based system comprising a processing unit and a non-transitory storage device storing instructions, which instructions when executed by the processing unit, configure the cloud-based system to perform a method according to any embodiment of the method aspects.

These and other aspects will be apparent including computer program product aspects where a product comprises a non-transitory storage device storing instructions that when executed by a processor configure the processor to perform any method herein. Further a meter set, such as a gas meter set, comprises: at least one sensing unit each positioned at a respective location of the meter set to be monitored to provide at least one sensing unit signal; and a locally located control unit configured to be coupled to the at least one sensing unit and further to communicate with a remotely located control unit; wherein the locally located control unit is configured to: communicate at least one sensing unit signal to the remotely located control unit to provide input data for detecting a condition from the respective location using the at least one sensing unit signal to trigger a communicating to at least one of one or more alarm signaling units an alarm signal in response to the condition. In an embodiment, the at least one sensing unit comprises a vibration sensor and the condition comprises an abnormality as described.

BRIEF DESCRIPTION OF DRAWINGS

FIGS. 7A, 7B and 7C are block diagrams of an oil monitoring system in accordance with examples.

FIGS. 8A, 8B and 8C are illustrations of rotary meters with a working condition monitoring system in accordance with examples.

FIGS. 9A and 9B are block diagrams of a working condition monitoring system in accordance with examples. The working condition monitoring systems of FIGS. 9A and 9B may be utilized with either example of the rotary meter shown in FIGS. 8A and 8B.

Figure 1:
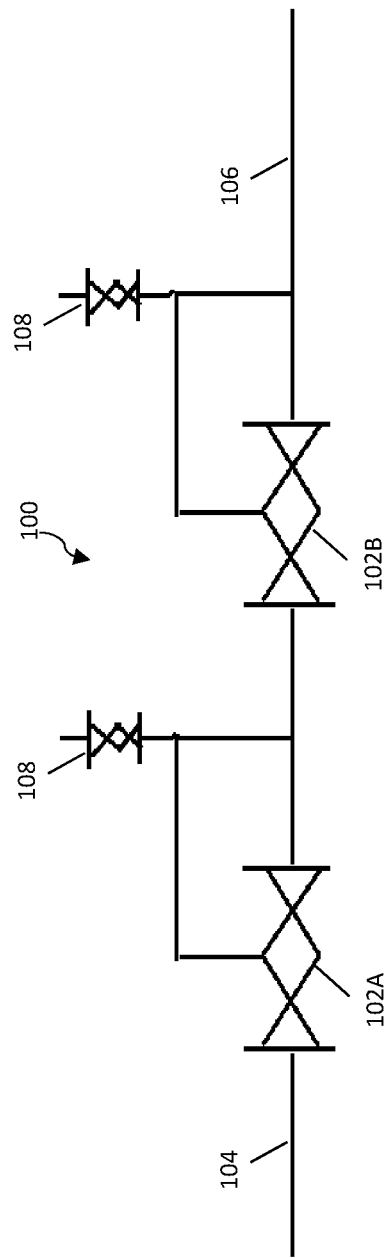
FIG. 1 is an illustration of a series overpressure protection in accordance with an example.

The present concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

DETAILED DESCRIPTION

The general inventive concepts described herein are not limited to any single context and may apply to various contexts or applications. In particular, while a natural gas context is described herein, a person of ordinary skill in the art will appreciate that other fluid distribution contexts may apply including other gases including mixed gases, water and oils. It will be appreciated that the examples herein are chiefly described in relation to natural gas measurement stations or meter sets. Such are typically located between a service line in a utility's distribution system and a customer's fuel run or customer piping system.

Natural gas or fossil gas is an odorless naturally occurring hydrocarbon gas mixture consisting primarily of methane, but can include varying amounts of other higher alkanes, and sometimes a percentage of hydrogen, carbon dioxide, nitrogen, hydrogen sulfide, or helium. Natural gas is used as a source of energy for heating, cooking, electricity generation, fuel for vehicles, as well as other processes in various industries. In order to assist utilities and consumers in detecting leaks, natural gas is odorized with a scent similar to rotten eggs. This odorization is accomplished by adding tert-Butyl thiol (t-butyl mercaptan) to the natural gas mixture.

Natural gas meter sets take natural gas from the utility's termination point of service and deliver it to the customer's gas system. In transit, the natural gas flows, under pressure, through various components including piping, an overpressure apparatus, and a measuring apparatus.

In some embodiments, natural gas is blended with another gas creating a mixed gas or blended gas. A common mixed gas comprises hydrogen mixed with natural gas. Such mixed gases, when combusted, produce lower carbon emissions. However, lower calorific content results from such gas blending. It is thus desirable to measure a ratio of gas blending and/or detect when a change in gas blending ratio occurs. Such a change may be measured by determining a change in gas density.

Respective gases have respective gas densities and gas density of a blended gas changes with the ratio of gases blended. Gas density impacts measurement of vibration e.g. frequency through the gas. It is desirable to know the ratio of specific gases, for example, for consumption purposes. Additionally, in embodiments, leak detection is responsive to the gas blend. Vibration signal thresholds are determinable such as from respective reference signals for respective gas blends. Leak detection is made responsive by using the appropriate vibration signal in accordance with the detected gas blend.

Meter Set Piping

Natural gas meter sets are constructed with steel pipes, various tubing, weld fittings, screwed fittings, flanges, gaskets, pressure ports, pressure reducing apparatuses, and measuring apparatus. The construction of a natural gas meter set creates the opportunity for leaks where these component parts are joined together.

Meter Set Measuring Apparatus

A measuring apparatus measures the flow of natural gas and may come in the form of a positive displacement meter or an inferential meter.

A positive displacement meter is a precision measuring instrument that is manufactured to tight tolerances. As natural gas flows into a meter, the natural gas fills and empties measuring chambers. The meter then counts the number of times this occurs and determines the volume of natural gas that flows through the meter. As the tolerance of the measure chamber changes, the accuracy of the meter could change as well.

An inferential meter is a precision measuring instrument that is also manufactured to tight tolerances. As natural gas flows into a meter, the natural gas flows through measuring chambers. The flow rate or velocity is measured either mechanically or electronically and compared to the area of the measuring chamber.

For both types of measuring apparatuses, particulates in natural gas can attach to different internal components of the meter and create resistance. This resistance increases the amount of pressure required to operate the meter and, therefore, reduces the outlet pressure of the meter.

Measurements in a measuring apparatus may be performed with the assistance of a processing unit. The unit may define an electronic volume corrector (EVC). The processing unit may be coupled to a communication unit and/or a display unit to communicate or otherwise present information.

Meter Set Overpressure Apparatus

An overpressure apparatus provides a form of relief from the potential overpressure of natural gas. A natural gas meter set may use one of three overpressure protection methods: series overpressure protection, monitor overpressure protection, and relief overpressure protection. Additionally, each of these three methods can be installed in combination and/or in parallel to improve reliability and prevent a customer shutdown during maintenance.

FIG. 1 shows an illustrative example of a series overpressure protection 100. This form of overpressure protection requires two or more overpressure apparatuses (102A, 102B) to be installed in series. Each apparatus helps reduce the meter sets inlet 104 pressure originating from the utility's termination point to a set delivery pressure at the customer's gas system. Each overpressure apparatus in the series has a different pressure setting. The first overpressure apparatus 102A reduces the meter sets inlet 104 pressure (i.e. service pressure termination) which is subsequently further reduced by the second overpressure apparatus 102B in the series. The last overpressure apparatus in the series reduces the pressure arriving from the previous overpressure apparatus to a level for the safe delivery of the natural gas to the meter set outlet (106) termination point, the customer's gas system.

If an overpressure apparatus fails, a small "tattle-tail" relief valve 108 releases natural gas into the atmosphere. Such a release of natural gas is used to alert a bystander or the customer to notify the utility of an odor of gas and subsequent failure of the overpressure apparatus.

Figure 2:
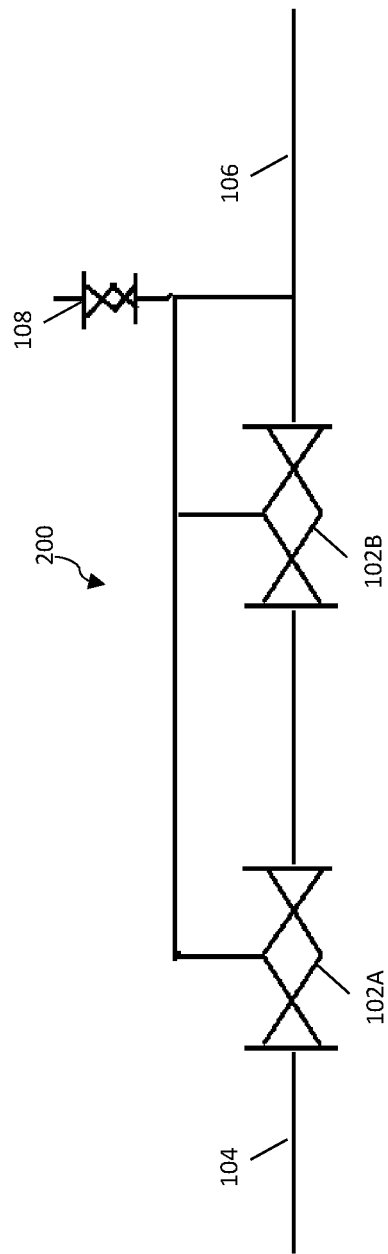
FIG. 2 is an illustration of a monitor overpressure protection in accordance with an example.

FIG. 2 shows an illustrative example of a monitor overpressure protection 200. Similar to a series overpressure protection 100, a monitor overpressure protection 200 requires two or more overpressure apparatuses (102A, 102B) to be installed in series. Each apparatus helps to reduce the meter sets inlet 104 pressure to a pressure level that can be safely delivered to customers. Although each apparatus is set at different pressures, they are all sensing one pressure. While the first overpressure apparatus 102A is reducing the meter sets inlet pressure, the second overpressure apparatus 102B and any additional overpressure apparatuses in the series are "monitoring" the pressure. If, however, the first overpressure apparatus 102A fails, the second overpressure apparatus 102B takes over control and begins reducing the meter sets inlet 104 pressure.

If the combination of overpressure apparatuses (102A, 102B) in a monitor overpressure protection 200 fails to sufficiently reduce the pressure, the monitoring apparatus takes control and a small amount of natural gas is released into the atmosphere by a small "tattle-tail" relief valve 108 positioned at the end of the series before the natural gas flows into the meter set outlet 106. Such a release of natural gas is used to alert a bystander or the customer to notify the utility of an odor of gas and subsequent failure of the overpressure apparatus.

Figure 3:
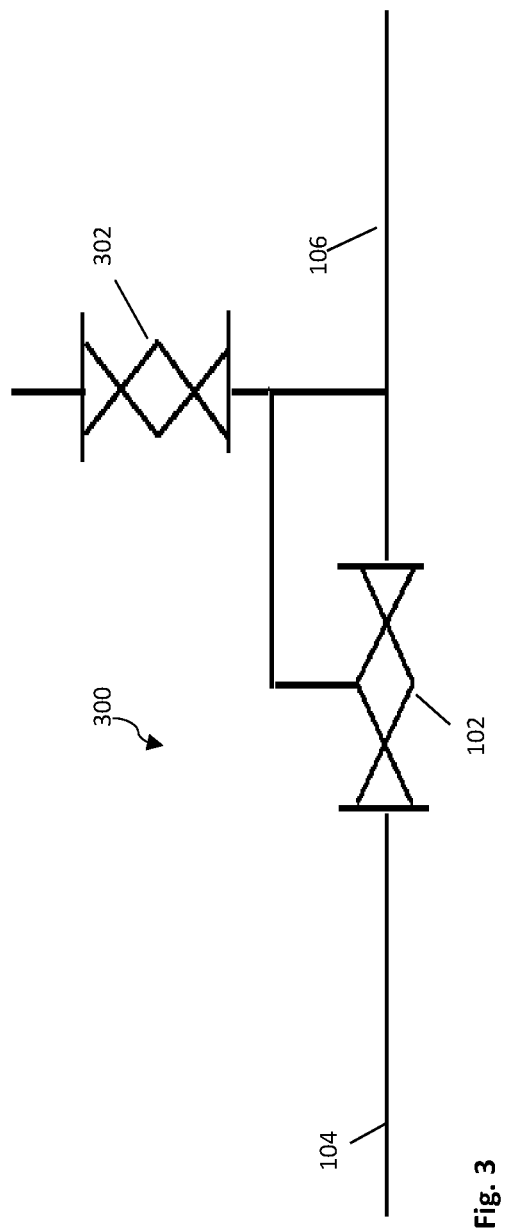
FIG. 3 is an illustration of a relief overpressure protection in accordance with an example.

FIG. 3 shows an illustrative example of a relief overpressure protection 300. This method of protection against overpressure involves positioning a single overpressure apparatus 102 that reduces the meter sets inlet 104 pressure to the meter set outlet 106 pressure for safe delivery to the customer's gas system.

In the event that the single overpressure apparatus 102 in a relief overpressure protection 300 fails, a large relief valve 302 releases natural gas into the atmosphere thereby reducing excess pressure.

For all three overpressure protection configurations (100, 200, 300), the backup mechanism for relieving excess pressure is the release of natural gas into the atmosphere. Given the highly flammable nature of natural gas, this creates a health and safety risk to the surrounding environment if left undetected. The dissipation of natural gas outside of the natural gas meter set is also wasteful and potentially costly from an economic perspective. Moreover, the release of the methane found in natural gas poses a threat to the ozone layer and the natural environment more generally. These concerns may be heightened in a relief overpressure protection 300 scenario where a large relief valve 302 is involved and potentially releasing large amounts of natural gas at any given time. Similar concerns exist for mixed gases.

In addition to these overpressure protection configurations (100, 200, 300) that cause natural gas to be released into the atmosphere, natural gas may be released elsewhere in a natural gas meter set. A natural gas meter set is comprised of all or some of the following components: rotary meter, turbine meter, ultrasonic meter, diaphragm meter, natural gas regulators, control valves, relief valves, electronic instrumentation, pipe fittings, and piping. The installation and fitting of these various component parts creates various opportunities for natural gas meter sets to release natural gas into the atmosphere.

Where there is an active natural gas leak, time is of the essence in minimizing the potential destruction to the surrounding area and natural environment. The same applies for other types of fluid leaks including oil spills. However, in order to control or stop the leakage, the leak must first be detected and then reported to the utility before the appropriate action can be taken.

In the absence of a monitoring system, detection of a natural gas leak largely depends on a customer or bystander to be in the surrounding area of the leak and close enough to smell the "rotten eggs" odor associated with t-butyl mercaptan. Moreover, this method of detection relies on the bystander's olfactory senses, his/her familiarity with the smell of t-butyl mercaptan, and his/her recognition that the detected odor is associated with natural gas which is itself odorless.

Other types of fluid leaks may similarly be difficult to detect in the absence of a monitoring system. For example, oil leaking from an underground pipe may go unnoticed by those above ground.

A monitoring system described herein overcomes many of the limitations associated with an olfactory-based mechanism of detecting a natural gas leak. In particular, it eliminates the need to have a bystander nearby who is capable of smelling t-butyl mercaptan and associating it with natural gas.

Likewise, a monitoring system described herein eliminates the need to visually detect a leak from a meter system thereby potentially allowing for the detection of a leak at a location in a meter system that is underground or otherwise not visible or easily accessible to the general population.

Condition Monitoring—Vibrations

The use of vibration sensors in a monitoring system may immediately detect an abnormality in the meter set caused by a fluid leak. By reliably and quickly detecting a fluid leak, a faster response may be effected in stopping the leakage which has the potential to reduce the likelihood and severity of an explosion.

Since meter sets have a natural frequency during various flowrates, a monitoring system that uses sensors to detect variations in the vibration of a meter set can assist in detecting fluid leaks. In particular, a meter set detected to have an abnormal frequency as compared to its natural frequency may be an indication that there is fluid leak.

A person of ordinary skill in the art would appreciate that natural frequencies occur in every object, structure and systems. Further, this natural frequency can be calculated for any particular object, structure or system. For example, the natural frequency of a simple oscillation can be defined as:

$$f=\omega/2\pi$$

Where $\omega$ is the angular frequency of the oscillation, measured in radians/second. The following expression defines the angular frequency:

$$\omega=\sqrt{(k/m)}$$

This means:

$$f=\sqrt{(k/m)}\div 2\pi$$

Where k is a spring constant and m is the mass.

By way of example, If k=100 N/m and m=1 kg, then the natural frequency is 1.6 Hz, which means this system would oscillate 1.6 times per second.

Vibration sensors are capable of measuring the condition of vibrations of an object, structure or system. By positioning vibration sensors throughout various locations of the meter set, the meter set can be monitored. In an embodiment, the gas mix can be monitored. In particular, the vibration sensors can monitor the meter set during normal and abnormal operations. The vibration sensors may measure vibration when gas at different blends are passed through. In an embodiment, observations may be made and respective baselines prepared (e.g. signals captured) and stored. In an embodiment, respective signals may be used to train a classifier.

The number and positioning of vibration sensors may depend on a number of criteria including the probability of a fluid leak, the amount of potential leakage in the event of a leak, the density of people and property in the surrounding area, and whether there are any other monitoring systems in place. For example, one may consider it appropriate to place vibration sensors at relief valves, and in particular at large relief valves, as these are points in the meter set that are designed to release natural gas in the event of an overpressure. One may also find it more appropriate to position vibration sensors along portions of the meter set that span a metropolitan area as opposed to a rural area.

An appropriate vibration sensor may be selected in accordance with the natural vibrational frequency of the component part of the meter set and the sensitivity necessary to detect an abnormal change. A vibration sensor may be connected to a processor or microprocessor that processes and adjusts the measurements and readings of the input vibration data including adjusting the sensitivity of the vibration sensor. An example of a vibration sensor is an accelerometer.

During normal activity, a vibration sensor detects the natural frequency of the associated component part of the meter set. The normal activity of a meter set would range from no flow to maximum flow for each utility customer's application. Based on this normal operational cycle of a meter set, a unique vibration pattern is generated for each meter set for each utility customer. This unique vibration pattern may define a normal "signature" and may be stored as baseline vibration data for comparing to (new) operational vibration data to detect a change such as a change in a natural frequency.

Respective unique vibration patterns at respective flow rates may be generated for mixed gases such as for ratios/percentages of hydrogen in natural gas (e.g. 0%, 5%, 10%, etc. to an expected maximum). More granular or less granular ratios/percentages may be utilized and may be determined such as by comparing the similarity of the vibration patterns generate.

A detected change in condition (e.g. in this natural frequency) may indicate abnormal activity. An example of an anomaly may be a detected frequency that exceeds a threshold frequency established based on the normal operational cycle of the meter set at that same particular location. Abnormalities in vibrations may be triggered by several different reasons including a) leaks in pipe, pipe fittings, regulators, control valve, relief valves, meters, and instruments; b) failure of internal components of regulators, control valve, and relief valves; c) failure of measuring apparatuses; d) vandalism of meter set; e) unauthorized use; and f) tampering. These various conditions may have one or more possible causes. For example:

Condition a): Stress in connections, Pipe dope failures and Mating surfaces stress;

Condition b): Seat failures, Diaphragm ruptures, Seals, Dirt on components, Vandalism; and Instrument connections;

Condition c): Meter locked up, Dirt in meter, and Bearing failure;

Condition d): Vehicle collision, Valves turned on/off, and Destruction;

Condition e): Increase/decrease pressure, and Alternative connection; and

Condition f): Turn on/off, and Index manipulated.

At component parts of the meter set where natural gas is designed to be released such as at relief valves, the abnormal vibration associated with the release of natural gas may be established in advanced such that a detection of that "signature" vibration would strongly indicate that the abnormality is a gas release. An abnormal "signature" vibration may be established by measuring the vibration during an intentional and time-limited release of fluid, or subsequently confirming that an abnormal vibration pattern was indeed caused by a gas leak.

A detected change in condition (e.g. in the natural frequency) may indicate a change in gas mix. In an embodiment, detection of such a change is used to signal an alarm (e.g. communicate information). However, in an embodiment, detection is used to adjust abnormality detection operations when abnormality detection is responsive to gas mix. For example, operations which compare the detected vibration signal to reference signal are adjusted to utilize the reference signal associated with the detected gas mix (e.g. a gas density).

Figure 4:
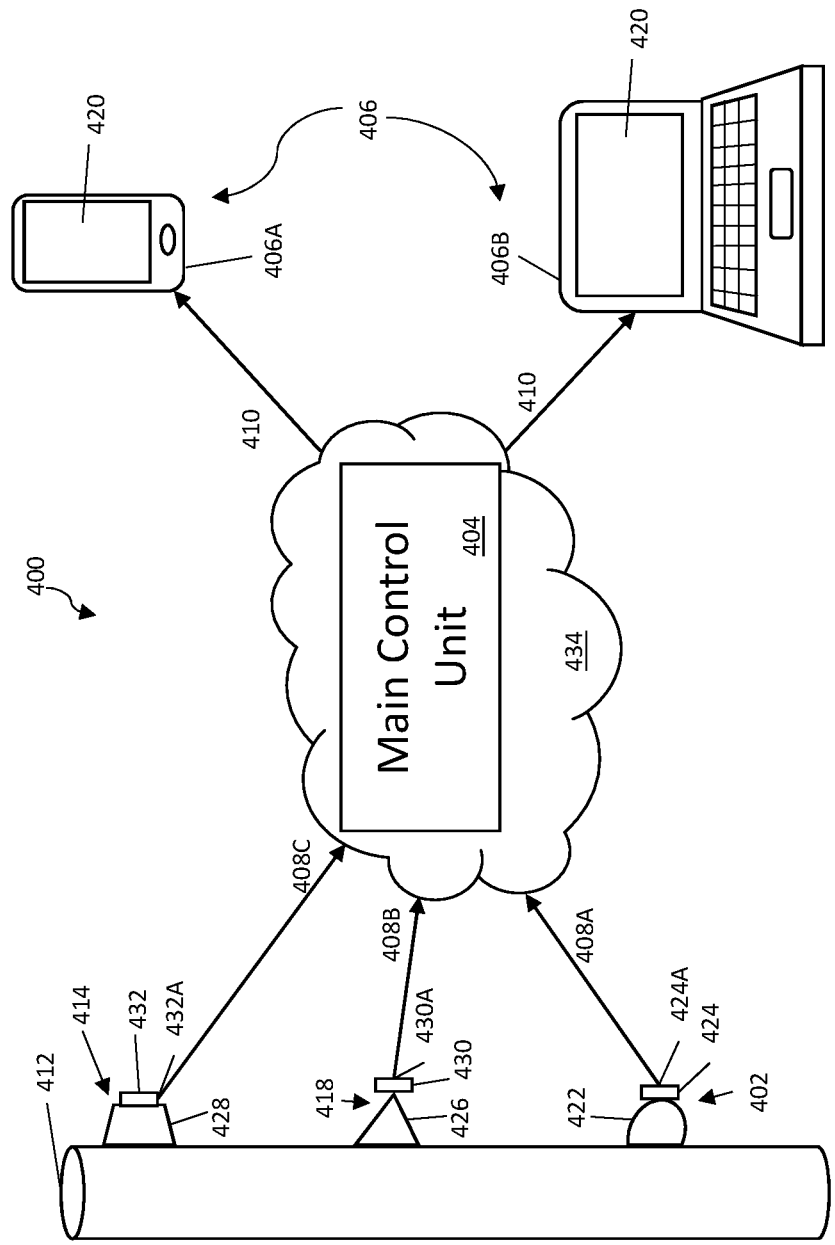
FIG. 4 is an illustration of a meter set monitoring system using vibration sensors in accordance with an example.

FIG. 4 shows an illustration of a meter set monitoring system according to an example. Meter set monitoring system 400 comprises at least one vibration sensing unit 402, main control unit 404, and one or more alarm signaling units 406. Vibration sensing unit 402 comprises vibration sensor 422 and a processor unit 424. Main control unit 404 relays communications between vibration sensing unit 402 and alarm signaling unit 406 which may be either or both of alarm signaling unit units 406A and/or 406B. Main control unit 404 may be connected to vibration sensing units 402 for one or more different meter sets 412.

In addition to vibration sensing units 402, other types of condition sensing units, such as pressure sensing unit 414 and oil condition sensing unit 418, each comprising of a different respective sensor 426, 428 and a respective processing unit 430 and 432, each processing unit 430 and 432 providing respective input data 408B and 408C, may be connected to main control unit 404. Pressure and oil condition monitoring are described in further detail with respect to additional figures herein below.

In an embodiment, the various devices herein (e.g. condition sensing units such as vibration sensing units 402, pressure sensing unit 414 and oil condition sensing unit 418, main control unit 404 and alarm signaling units 406A and 406B) comprise respective communication components (424A, 430A and 432A). The respective communication components (424A, 430A and 432A) communicate via one or more networks 434, which may be wired and/or wireless based networks, and in accordance with one or more protocols, which networks and/or protocols are as is known. The networks 434 may include a public network such as the Internet. Main control unit 404, by way of example, may be provided as a cloud-based service, which may be configured as a software as a service (SaaS) model.

In an embodiment, the respective vibration sensing units communicate respective vibration signals to main control unit 404 independently of each other and any associated meter set. For example, communication is without communicating via a processing unit or a communication component of a meter set, such as a meter set monitored by the respective vibration sensing units.

It will be understood that main control unit 404 comprises a computing device having various components coupled for communication including at least some of: processor(s) (e.g. CPU, GPU, etc.), storage device(s), one or more communication subsystems or devices, display(s), input device(s), output device(s), etc. Displays may be touch or gesture enabled. Input devices may include a pointing device such as a mouse, a microphone, a camera, a keyboard, button(s), etc. Communication devices may provide any of wired or wireless communications and may be short or long range. Communication devices may couple to a location device such as to provide satellite based location services. Output devices may include a speaker, lights, vibration/haptic devices. The various components may be coupled via one or more communication buses or other structures.

The storage devices may store instructions and data for example, which instructions when executed configure the operation of the computing device. The instructions may define an operating system, applications, etc. The computing device for main control unit 404 may be configured as a server or other device configuration.

In an embodiment, main control unit 404 receives respective meter set data (not shown) including flow rate data determined by a respective meter set. In an embodiment, a web interface (not shown) is provided for data received by main control unit 404 and alarms detected. Data provided by the interface may comprise meter set data and input data (e.g. sensor data) including input data 408A, 408B, 408C. The web interface may be provided to alarm signaling units 406 or other devices (not shown).

In an embodiment, the web interface comprises a graphical user interface (GUI) comprising a layout or map of components of a distribution system where the components comprise at least some of meter sets, pipes, pipe fittings, regulators, control valves, relief valves, and instruments and respective sensors. In the GUI, controls are provided in association with at least some components. Controls are configured to receive input to perform one or more of: presenting sensor data; presenting flow rate data; presenting alarm signals; activating a further interface (e.g. overlay or screen of a GUI) for additional information (e.g. such information may comprise prior sensor data and/or prior meter set data, particulars about the associated component such as make, model, etc.) In an embodiment, at least some of the controls are gesture-based controls, for example, to receive a tap to activate or invoke the control.

In an embodiment, rather than via a web interface, data is provided by main control unit 404 to any of the respective alarm signaling units 406 or other devices via an application programming interface (API) for use by an application stored and executed by a respective device. Of course, main control unit may be configured with both a web interface and an API to serve an application. The GUI may be configured as a dashboard as described further herein below.

Any of the processing units 424, 430 and 432 herein may be computing devices such as described. Other computing devices (e.g. other processing unit types) may be used such as programmable logic devices, which may be field programmable such as a field programmable gate array (FPGA), etc.

In one embodiment, the input data 408A communicated from the vibration sensing unit 402 to the main control unit 404 is vibration data. In another embodiment, processing unit 424 of the vibration sensing unit 402 processes the vibration data from the vibration sensor and transmits input data 408A comprising alarm data to the main control unit 404. Vibration sensing unit 402 may communicate alarm data and vibration data (signals).

Main control unit 404 that receives input data 408A comprising vibration data (e.g. similar to raw vibration data and in contrast to a processed alarm signal or a condition of vibration, determined by local processing unit 424, for example) may further process that data to a condition of vibration before communicating the condition of vibration as output data 410 to one or more alarm signaling units 406. For processing of the vibration data to generate a condition of vibration, the main control unit 404 accesses a stored baseline vibration data established as a normal "signature" of the meter set and compares the input vibration data (e.g. 408A) to this stored baseline vibration data. Alternatively, main control unit 404 accesses a stored abnormal vibration data established as a "signature" of the meter set during abnormal operations and compares the input vibration data for a potential match. Main control unit 404 may use an algorithm or a set of rules for determining a condition of vibration for the received vibration data (e.g. 408A).

As noted, in an embodiment, selection of the baseline vibration data is responsive to a current gas blend. In an embodiment, a current gas blend may be input to main control unit 404 such as by an operator. Gas blend information may be received from a gas supplier, as an example. Alternatively or in addition a current gas blend may be determined from vibration data. In an embodiment vibration data is evaluated to determine the gas blend (or a change in gas blend) such as by comparison to at least one reference signal. In an example, a matching algorithm may be employed to compare to a current vibration signal with one or more stored reference signals.

Through observation, as an example, where there are multiple vibration sensors, one of the respective vibration sensors may signal vibration data that is more responsive to gas blend ratio and the respective signal may be used when comparing to determine the gas blend or change in gas blend. Further, a determination of gas blend using one respective vibration sensor may be applicable for multiple meter sets or other distribution system components related to the meter, etc. as the components are related since they all distribute a same gas blend from a same source—there is no blending within the related portion of the distribution system.

Main control unit 404 may use machine learning for determining a condition of vibration. For example for determining a condition of vibration, main control unit 404 may implement a classifier. Suitable classifiers types include: Linear classifiers such as Logistic Regression, Naive Bayes and Perceptron; Decision Tree and Random Forest; Kernel estimation (e.g. K-Nearest Neighbor); Support Vector Machines, and Artificial Neural Networks/Deep Learning; among others. In an example, supervised learning may be performed to train a classifier, providing vibrations signals representative of normal operations and abnormal operations. The signals may be obtained from real world measurements or simulated measurements or both.

After a main control unit 404 has processed a condition of vibration, if that condition of vibration is programmed to activate an alarm signaling unit 406, main control unit 404 sends an alarm signal as an output data 410 to the alarm signaling unit 406. An example of an alarm signaling unit comprises a smartphone 406A, a computer/laptop 406B, or any other mobile device. The alarm signal may be sent to an alarm signaling unit 406 in the form of a text message, email, phone call or other protocols. The alarm signal may also come in the form of changes on a dashboard 420. Routing of the alarm signal may be directed to devices that are subscribed or otherwise set-up to receive such an alarm signal. Different devices can receive different alarm signals which may depend on the device type and/or the user preferences.

If the condition of vibration received by an alarm signaling unit 406 is determined to be triggered by a fluid leak, the alarm signaling unit 406 may activate an alert signaling that there is a fluid leak in proximity to the vibration sensing unit 402 that provided the vibration data.

The processing of the vibration data by main control unit 404 may involve transforming the data to a standardize message depending on the significance of the data. For example, based on the vibration data, it may be determined that there is a low, medium, or high likelihood of an active fluid leak. This processed data may then be sent to the alarm signaling unit 406 accordingly. Personnel (e.g. a user) monitoring the alarm signaling unit 406 can view the processed vibration data or condition of vibration on the dashboard and determine whether a response is appropriate or necessary.

In another embodiment, the alarm signaling unit 406 is integrated with a user's smartphone 406A (other mobile device such as a tablet, etc., though the form of device is not limiting). The dashboard displaying the processed vibration data or condition of vibration is configured to appear in a mobile application (e.g. a native application dedicated to the monitoring system that is installed and executing on the user's mobile device or a web browser) accessed using the user's mobile device. Such an embodiment could similarly alert users of a fluid leak such as a natural gas leak, but it may also advise a user to evacuate based on the geographical location of the customer relative to where the potential leak is detected. It may also automatically connect the user to the utility for any necessary support.

While alarm signaling unit 406 may communicate via a dashboard type interface of a user application, as noted above, monitoring information such as an alarm or condition data etc., may be communicated through other channels such as: a push notification associated with a user application, email, text or short message service (SMS) or other variants thereof, voice (e.g. cellular voice call, voice over internet protocol (VOIP)) or another channel.

It is understood that the smartphone 406A and computer/laptop 406B are other examples of computing devices as described herein.

In another embodiment where alarm data is received by main control unit 404, main control unit 404 may either relay that data as an alarm signal to one or more of the alarm signaling units 406 or wait for a secondary trigger such as another input of alarm data. An aggregate approach to activating an alarm signaling unit 406 may involve processing for false alarms and/or receiving two or more input alarm data within a certain period of time.

As noted, each of the alarm signaling units 406A and 406B may have a display device or to present a dashboard 420, a type of application interface, which typically comprise a graphical user interface and may include sound or be configured to receive sound (e.g. voice commands). As noted, the dashboard may be web-based or application-based.

In one embodiment, the vibration sensing units are connected to a local alarm signaling unit which may be a display or other output device of or coupled to local processing unit 424. Once a vibration sensing unit detects a frequency that is considered abnormal by the main control unit, the local alarm signaling unit is activated to alert the surrounding area that there is a potential fluid leak. The alarm signaling unit may alert the surrounding area using one or more senses including visual, auditory, or olfactory cues. For example, once activated, the alarm system may cause lights to flash, a siren to blare or a higher concentration of t-butyl mercaptan to be released. The connection between the vibration sensing unit, the main control unit, and the local alarm signaling unit may be wired, wireless or any other type of remote connections.

In another embodiment, the vibration sensing units are connected to an alarm signaling unit in a remote location (not shown). This remote alarm signaling unit may be monitored by a personnel (user) who is in a position to respond. For example, the remote location may be the location of the utility and the personnel is affiliated with the utility. Once triggered, the personnel can take appropriate action to respond to a potential fluid leak including sending technicians to seal the source of the fluid leak.

In addition or in the alternative to alarm signals related to gas leaks or operational abnormalities (tampering, etc. such as is listed), alarm signaling units 406, for example, via dashboard 420, may receive gas blend information including gas bend change data, which may comprise an alarm signal.

Figure 5:
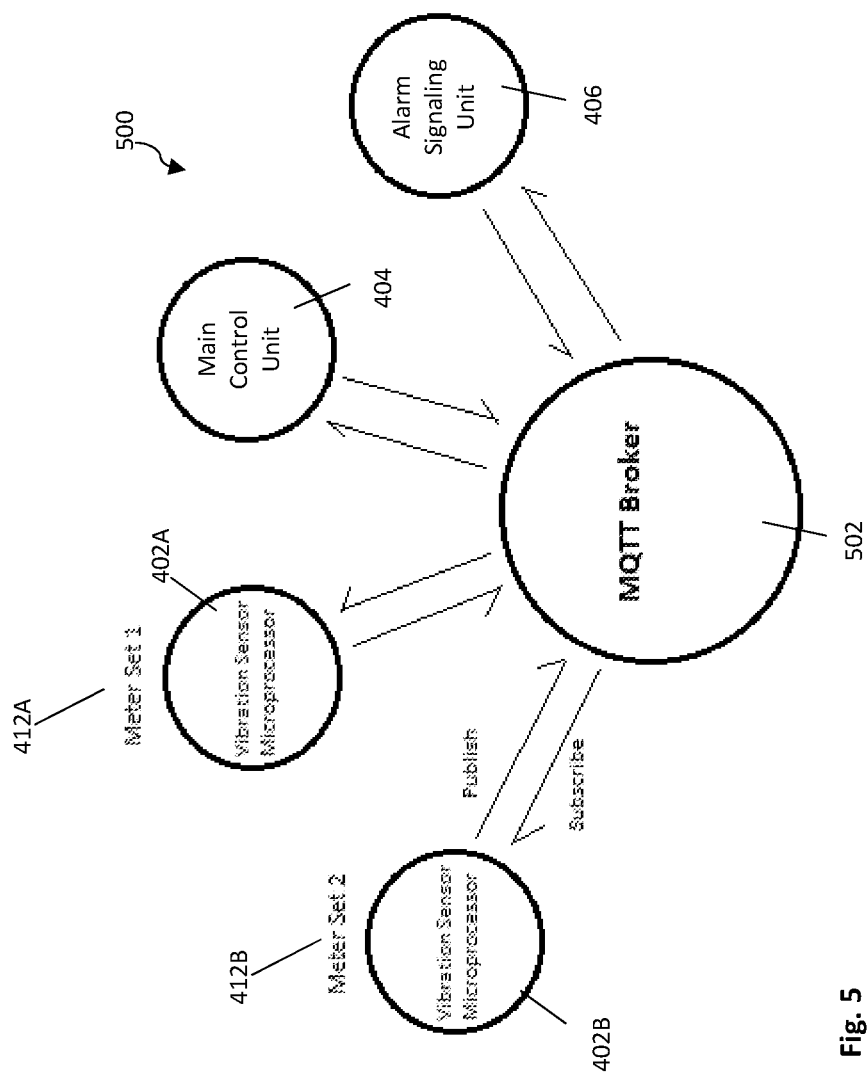
FIG. 5 is an illustration of a meter set monitoring system using vibration sensors in accordance with an example.

FIG. 5 shows an illustration of a meter set monitoring system using vibration sensors integrated with a Message Queuing Telemetry Transport (MQTT) broker according to an example. In this exemplified embodiment, a meter set monitoring system 500 is comprised of two vibration sensing units (402A, 402B), each positioned at a different meter set (412A, 412B), a MQTT broker 502, a main control unit 404, and an alarm signaling unit 406. A MQTT broker 502 is a computing device comprised of hardware and software and may include a server configured to provide message brokering services using a publish/subscribe protocol to transport messages between devices. For example, it may be configured to use MQTT protocol such that any alarm signaling units 406 including customer devices and vibration sensing units 402 subscribed to the MQTT broker 502 may communicate with each other by sending and receiving MQTT messages. A single MQTT broker may be connected to one or more different meter sets 412 each acting as MQTT clients. While a MQTT broker is described, an other messaging middleware component may be employed.

To activate the alarm signaling unit 406, a vibration detected by a vibration sensing unit 402 positioned at the location of meter set 412 publishes the vibration data to the MQTT broker 502. In an example, the vibration sensor is positioned on meter set 412. A main control unit 404 that has subscribed to the MQTT broker 502 receives the vibration data, processes it to a condition of vibration, and then depending on the condition, may publish the condition back to the MQTT broker 502. An alarm signaling unit 406 that has subscribed to the MQTT broker 502 may receive the condition of vibration from the MQTT broker 502 as an alarm signal thus activating the alarm signaling unit 406.

In addition to vibrations, other conditions may be detected in the meter set including an oil condition and working condition. A condition is any property or characteristic of a fluid or meter system that may be an indicator of its status, activity or health. Different types of sensors may be used to detect different conditions, and more than one condition may be detected in a monitoring system. Options for sensor units e.g. pressure sensing unit 414 and oil condition sensing unit 418) are described below.

Condition Monitoring—Oil

Oil level monitoring can be implemented using a sensor such as a level switch selected for the task at hand and keeping in mind the working environment. An appropriate sensor may be selected in accordance with an appropriate size to function in the expected temperature range and pressure range, etc. Different types of sensors may be useful for such a task. Three different types of level switches, typically of a miniature size, that may be employed are an ultrasonic level switch; floater level switch; and optical level switch. Examples may include non-contact liquid level switches such as are available from numerous suppliers including ABB™, Siemens™, Thermo Scientific™, Endress+Hauser™, AMETEK™, Clark-Reliance™, GEMS™, GHM™, and Sitron™. A miniature float sensor may be available from Flowline™, Baker™, Dwyer™, APG™, Madison™, etc.

Oil monitoring may be implemented in an electronic gas meter platform. The electronic meter may be configured to determine the oil level measurement on a daily (or other periodic) basis. A period or other schedule may be chosen with a view to minimizing any extra power consumption due to the making of the measurement. Often the electronic meter platforms are battery powered rather than line powered due to their location in a facility.

While a single sensor may be used to measure oil consumption, such a single point of measurement may not be sufficient to achieve desired results. Rotary meters may be configured for mounting in a user selected horizontal or vertical orientation. Selectability provides flexibility and reduces requirements to have inventory of different types of meters. However, dedicated horizontal or vertical meters may be configured as well. For a selectable meter, a plurality of sensors, for example, four switches, may be mounted in locations within the meter that achieve measurement goals for sensing oil in particular chambers of the meter and when the meter is in a specific orientation. By way of example then, four oil level sensors may be positioned such that a first pair of the sensors are in a (magnet) metering housing chamber (e.g. a metering chamber) and another pair are in a thrust chamber. One of each of the pairs is positioned for sensing oil when the meter is in a horizontal position and the other of each of the pairs is positioned for sensing oil when the meter is in a vertical position. In a dedicated horizontal or a vertical meter, a single sensor per chamber may be employed, for example, with one in each of two chambers. The position of the sensor therein may be in accordance with the type of sensor used. The sensors can be positioned in either of low or high position (e.g. relative to gravity) as may depend on the type of sensor used.

In addition to or as an alternative to oil level monitoring (indicating oil consumption), other meter parameters may be monitored that are indicated by oil properties. Oil colour, clarity, aeration (e.g. foaming), meter corrosion, varnish, wear debris, or other quality monitoring indicative of meter health may be signaled using sensors such as spectrometers. One or more spectrometer(s) may be mounted to measure oil properties and provide signals (e.g. data) to a control unit. The data representing the oil properties may be stored, evaluated and an alarm may be triggered. The data and/or alarm may be communicated via a communication interface. The data may be processed (e.g. averaged, conditioned, etc.) prior to evaluation such as against one or more comparative thresholds, baselines, operating ranges, etc. Aspects of the oil level monitoring apply to oil condition monitoring as well be understood to a person of ordinary skill.

Various types of spectrometers may be employed including one or more of colorimeters, UV spectrometers and IR spectrometers. A rotary meter may have more than one oil reservoir (location for measuring an oil condition). It may be that one type of spectrometer is used in one oil reservoir and another type is used in a second reservoir. Applicable spectrometer configuration and baseline data may be stored such as on a storage device for a control unit (e.g. processing unit) of the rotary meter to enable use and measuring via the spectrometer(s).

Figure 6:
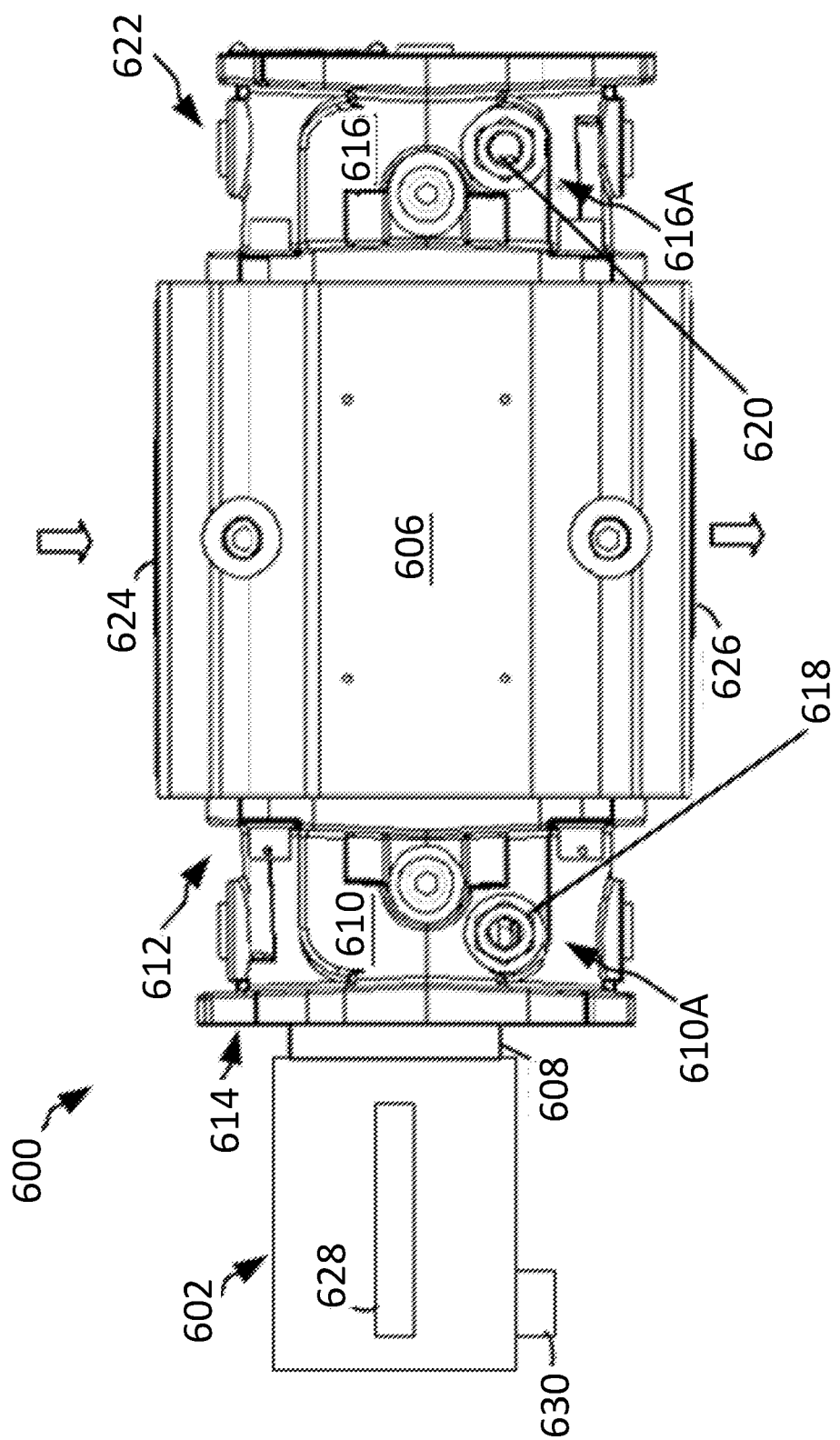
FIG. 6 is an illustration of a rotary meter with oil monitoring in accordance with an example.

FIG. 6 shows an embodiment of a rotary meter 600 in a vertical meter mount with an electronic gas meter platform 602. Electronic gas meter platform 602 provides a primary control unit for the rotary meter. Electronic gas meter platform 602 may provide a foundation of an oil monitoring system, defining a primary control unit therefor as well. Electronic gas meter platform 602 has a platform housing 604. In FIG. 6, platform housing 604 is mounted to a rotary meter housing 606 of meter 600 via a mounting bracket 608. As shown in FIG. 6, mounting bracket 608 may couple to a (e.g. magnetic) metering housing 610 on one end of rotary meter housing 606. Internally to metering housing 610 there is a chamber 612 having a metering unit 614 that is responsive to the rotation of a shaft driven by a rotary impeller in rotary meter housing 606 to measure a flow of fluid through the rotary gas meter 600. The metering unit 614 is used to provide rotational information. In a present embodiment it is a magnetic unit however a metering unit to provide rotational information includes, in other embodiments, an optical reader, an encoder, a pin wheel etc.

On the side of rotary meter housing 606, opposite from metering housing 610, is thrust housing 616. In each of the metering housing 610 and the thrust housing 616 are respective oil reservoirs 610A and 616A where oil is collected as a result of oil consumption within the rotary meter 600. A pair of sensors 618 and 620 are shown on respective faces of metering housing 610 and thrust housing 616 for sensing oil in the respective locations of oil reservoirs 610A and 616A. It will be understood that though one sensor is shown in the respective locations, more than one sensor may be used such as to measure and monitor more than one property. For example, it may be preferred to use a particular sensor for oil level monitoring and a particular sensor for other parameter monitoring.

Though not shown, rotary meter 600 may be configured for horizontal mounting, where the meter 600 is rotated 90° relative to FIG. 6. A pair of oil sensors (not shown) may be mounted via respective other faces of metering housing 610 and thrust housing 616. A position of electronic gas meter platform 602 may be adjusted for viewing when in horizontal mounting. In another embodiment (also not shown) a selectable configuration for mounting in either orientation may be provide having four sensors in respective pairs that are positioned so that there are two sensors in each chamber. One (or more) sensor in each chamber is positioned for horizontal orientation and the others are positioned respectively for vertical orientation.

Oil sensor 618 is mounted for sensing an oil level in chamber 612 within metering housing 610. Oil sensor 620 is mounted for sensing an oil level in a thrust chamber 622 internal to thrust housing 616. Though not shown, sensor wiring (e.g. running externally to respective housings 610 and 616) may couple the sensors 618 and 620 to platform 602. As noted oil sensors 618 and 620 may be mounted for sensing other oil properties. Additional oil sensors may be mounted (not shown).

Rotary meter 600 is configured for vertical orientation. That is, meter 600 has flow inlet 624 and outlet 626 vertically aligned such that a fluid (e.g. a gas) flows vertically through the meter.

FIGS. 7A and 7B show block diagrams of oil monitoring system 700 and 720 in accordance with examples. In FIG. 7A, oil monitoring system 700 comprises electronic gas meter platform 602 and two sensors 618 and 620 for monitoring oil level such as in two different chambers, for example, in accordance with rotary meter 600 of FIG. 6. It is understood that other parameters may be monitoring using applicable sensors.

In FIG. 7B, oil monitoring system 720 comprises electronic gas meter platform 602 coupled to two pairs of oil level sensors 616A/616B and 618A/618B. In this embodiment, the rotary meter is configured for selective orientation. Sensor 616A is positioned in a first chamber for horizontal orientation and 616B is positioned in the same (first) chamber for vertical orientation. Sensor 618A is positioned in a second chamber for horizontal orientation and 618B is positioned in the same (second) chamber for vertical orientation. It is understood that other parameters may be monitoring using applicable sensors.

In FIGS. 7A and 7B electronic gas meter platform 602 may be defined as a computing device as described above. The particular examples of components, protocols and configurations, etc. described further in respect of the electronic gas meter platform 602 for oil condition monitoring or otherwise may be adapted for other monitoring such as meter set monitoring using vibration.

More particularly, by way of example, electronic gas meter platform 602 comprises a processor 702, a storage device 704 as well as user interface 628. Processor 702 is coupled electronically to storage device 704 and user interface 628. Electronic gas meter platform 602 (e.g. processor 702) may be coupled to other sensors or components (e.g.

magnetic meter 613) for other measurements, etc. Electronic gas meter platform 602 may further comprise wired communication interface 630 which is coupled electronically to processor 702. In other embodiments magnetic operation is replaced with optical or mechanical operation as described.

Each of the user interface 628 and the wired communication interface 630 provide an alarm signaling interface controllable by processor 702 to signal an alarm, whether remotely and/or locally to the rotary meter. An on-board (relative to platform 602) wireless communication interface (not shown) is another example of an alarm signaling interface and it may be electronically controlled by processor 702.

Processor 702 may be a microprocessor, a microcontroller or other. Processor 702 may be implemented as a processor core, central processing unit (CPU) or other.

Storage device 704 may comprise a memory such as a programmable memory, for example, an electrically erasable read-only memory (EEPROM).

User interface 628 may be any one or more of a display screen, a light, a bell or other output device that may signal an alarm. It may be preferred to display the differential pressure value and/or alarm.

Electronic gas meter platform 602 may also comprise a wired communication interface 630, as noted, such as for communicating data including differential pressure data and/or alarm data. Wired communication interface 630 may be a component of the electronic gas meter platform. Wired communication interface 630 may be coupled to a short range and/or long range communication device (not shown) providing an external communication device. Short range and/or long range communication device may comprise an antenna and associated circuits. In an example, not shown, either short range or long range communication device may be on-board and internal to the rotary meter 600. A short range and/or long range communication device may be configured to communicate using known protocols or standards such as to communicate short message service (SMS) messages/text messages via a cellular network, messages via a Bluetooth™ network or Zigbee™ network, etc. (Bluetooth is a trademark of Bluetooth SIG, Inc. Zigbee is a trademark of Zigbee Alliance). Such messages may be alarm messages or data reporting messages or both. Wired communication interface may comprise a universal serial bus (USB), RS-232, Ethernet or other standard interface or a proprietary interface. Wired communication interface 630 may communicate differential pressure data as well as other data. Such may also provide access to storage device 704 such as for providing programming. However other interfaces or means to program storage device 704 may be provided.

In operation, the oil sensors may have open-collector output such that the sensor is open (high) when the oil level is low. Such sensors are easily combined such as for use in a selectable meter orientation configuration where pairs of sensors in each chamber are wired-AND. FIG. 7B shows each of the respective pairs in a wired-AND configuration (e.g. using gates 632A and 632B) to provide input to processor 702.

In such a configuration, one sensor will be always open due to the orientation, the other sensor for the corresponding mounting orientation will be closed (low) if the oil level is OK. But in the case that the oil level is low, both sensors will be open (high), and the output of wired-AND will be high. The electronic meter can detect this wired-AND logic as an oil level low signal for each chamber. In another example (not shown), logic may be used to effectively AND the respective signals within processor 702.

The electronic meter platform 602 may OR the two oil level low signals from different chambers (e.g. using an OR gate 634 (as in FIG. 7A) or logic) to have one oil level low alarm. An OR gate may combine signals from gates 632A and 632B of FIG. 7B. The electronic meter platform 602 will send an alarm pulse (e.g. control one of the interfaces 628, 630) when oil level the low alarm is triggered. The user interface may be controlled such as to display and/or sound an alarm and/or communicate the alarm to another device. The wired communication interface 630 may be controlled to communicate the alarm through a short message (or other message type) if the electronic gas meter platform 602 is so equipped.

The electronic meter platform 602 may control a logging of the alarm in alarm log (e.g. in storage device 704). The storage device may be controlled to log the alarm. Various logging techniques and practices may be used to record and/or report data such as at specific time intervals (e.g. every 15 minutes, every hour, etc.). A log entry may include data representing specific values and flags such as an alarm flag where a flag may be dedicated to an oil level alarm.

It is also understood that the oil monitoring systems 700 and 720 may be adapted to receive respective signals at processor 702 from two or more types of sensors such as to measure multiple parameters. FIG. 7C shows an adaptation of system 300 defining an oil monitoring system 740. In system 740, processor 702 receives oil sensor signals from sensors 618 and 620, similar to the configuration of system 700, as well as oil sensor signals from sensors 742 and 744. Sensors 742 and 744 may comprise spectrometers mounted to sense oil parameters (conditions) at respective locations 610A and 616A.

Each sensor 618, 620, 742 and 744 may provide its own input signal. For example, an oil level signal (measured by an applicable switch) may be receive separately from an oil condition signal (measured by a spectrometer). As shown, multiple oil level sensors may be employed where each reservoir may have one (FIG. 7A, 7C) or more such sensors (e.g. FIG. 7B). Similarly, multiple spectrometers may be employed where each reservoir may have one (FIG. 7C) or more such sensors (not shown). While the multiple oil level sensors may be coupled to processor 702 via one or more AND gates (FIG. 7B) when two or more such sensors are measuring oil level at a single oil reservoir given the binary nature (on or off) of the oil level signal, it may not be logical to combine the spectrometer signals using such gating. Each spectrometer signal may be received individually. The spectrometer signals may be combined using an OR gate 746 (or logic) such as is described in relation to OR gate 734. This configuration may be useful when the rotary meter is configured for selective horizontal or vertical orientation and the pooling (or other positioning) of oil in a respective reservoir may vary due to the orientation.

Processor 702 of the oil monitoring system may be programmed to periodically wakeup to read the oil sensor signal(s). Other measurements (readings and/or calculations) may also be performed at wakeup. Some measurements may be more frequently made than other measurements.

It will be understood that processor 702 may provide oil sensor signals and/or alarm signals as input data 408C to main control unit 404, which main control unit may process such data and/or relay alarm signals similarly as described in respect of vibration data and leak detection and gas blend detection. Processing aspects described for processor 702 whereby spectral image data from sensors is processed, comparing to baselines and thresholds, etc. may be configured into main control unit 404.

Condition Monitoring—Working, Pressure

Alternatively or additionally, a working condition may be monitored using a monitoring system described herein. FIGS. 8A-8C show a rotary gas meter 800 having an electronic gas meter platform 802. Electronic gas meter platform 802 provides a main control unit for the rotary meter. Electronic gas meter platform 802 has a platform housing 804. In FIGS. 8A and 8C, platform housing 804 is mounted via a mounting bracket 805 to a rotary meter housing 806 of meter 800. In FIG. 8B, platform housing 804 is unmounted and may be mounted remotely such as to another structure (not shown). The mounting bracket 805 may couple to a metering housing 807 on one end of rotary meter housing 806. Internally to metering housing 807 there is a magnetic metering unit 813 that is responsive to the rotation of a shaft driven by a rotary impeller in rotary meter housing 806 to measure a flow of fluid through the rotary gas meter 100. Magnetic metering unit 813 may comprise a Weigand sensor as a rotation counter sensor 813A. As previously noted, a metering unit such as unit 813 may comprise, in other embodiments, an optical encoder, a pin wheel, etc.

Electronic gas meter platform 802 may provide a foundation of a working condition monitoring system 803, defining a main control unit. Working condition monitoring system 803 may comprise, in accordance with a differential pressure monitoring embodiment as shown, one differential pressure sensor (e.g. a differential pressure detecting unit) having local pressure sensors and pressure leads extending to rotary meter housing 806. FIG. 8A shows pressure leads 808A, 808B extending to remote pressure connectors 810A, 810B on rotary meter housing 806 near ports 811A and 811B. Pressure sensors (not shown) coupled to the leads 808A, 808B are mounted inside electronic gas meter platform 802. Pressure leads 808A, 808B extend from local connectors or local ports 812A, 812B of electronic gas meter platform 802. Pressure leads 808A, 808B extending to remote pressure connectors 810A, 810B may, respectively, may define a first pressure communication assembly (808A/810A) and a second pressure communication assembly (808B/810B).

In FIG. 8B the working condition monitoring system 803 has two electronic leads 809A, 809B leading to ports 811A, 811B on rotary meter housing 806 to connect to electronics inside rotary meter housing 806. A processor of the electronic gas meter platform 802 may determine the differential pressure.

In FIG. 8C, the two electronic leads 809A, 809B extend to magnetic metering housing 807 and through ports therein (not shown).

In FIGS. 8A-8C, the respective pressure sensors measure pressure respectively at separate locations inside rotary meter 800, namely at an inlet 814 and an outlet 816 of the housing 806 through which the fluid flows. As such, the mounting location of the pressure sensor, per se, is not important as is where the pressure is taken inside the housing. In the embodiments, a first pressure communication assembly (e.g. sensor and leads, etc.) and a second pressure communication assembly (e.g. sensor and leads and/or conduit, etc.) communicate pressure information for the separate locations within rotary meter 800 to be monitored. In one embodiment (e.g. FIG. 8A), the information is a fluid signal and in the others (e.g. FIGS. 8B and 8C) an electronic signal.

In another embodiment, for example, where platform 802 is not directly mounted to the magnetic housing 807, platform 802 may receive a different kind of volumetric pulse input. Platform 802 may receive an input such as from a mechanical gas meter counter or another electronic gas meter counter, which may be directly mounted to the magnetic housing 807. These input pulses have a similar function as the pulses picked up by the magnetic sensor and platform 802 can calculate the flow rate in a similar manner the in the direct-mounted platform. A difference between these direct-mounted and remotely located embodiments may be that a frequency of the pulse input is much lower than in the direct-mounted platform. In such an example, platform 802 cannot perform a very accurate and in-time flow calculation. As earlier described, in other embodiments, magnetic operation may be replaced by optical or mechanical operation.

Examples of a differential pressure sensor are PC11D (WTP10) Differential pressure sensor from Nanjing Wotian Technology Co., Ltd. and DP86 differential pressure sensor from TE Connectivity Ltd. An example of a pressure sensor is a WTP series pressure sensor from Nanjing Wotian Technology Co., Ltd. It may be desired that a differential pressure sensor measures with accuracy to ±0.05 inches of water column ((w.c.) or an equivalent measure and a range of 0 to 24 inches of water column).

The differential pressure sensor or pressure sensors may be selected for use in accordance with the expected measurement range, environment, etc. expected for the task. Such parameters may comprise expected temperature range, differential range, resolution, error, and common pressure range for the meter installations and configurations.

With reference again to FIGS. 8A-8C, electronic gas meter platform 802 may provide a user interface 818 such as for displaying measurements and/or alarms, etc. as further described. Electronic gas meter platform 802 may provide a wired communication interface 820 as further described.

FIGS. 9A and 9B show block diagrams of a working condition monitoring system 900 and 920 in accordance with examples. In FIG. 9A, working condition monitoring system 900 comprises electronic gas meter platform 802 having a differential pressure sensor 902 coupled to pressure leads 808A, 808B for taking pressure remotely. Differential pressure sensor 902 provides a differential pressure detecting unit to detect and provide the differential pressure.

In FIG. 9B, differential pressure monitoring system 920 comprises electronic gas meter platform 802 coupled to the two pressure sensors 910A/910B via electrical leads 809A, 809B. Working condition monitoring system 920 is defined without a differential pressure sensor 902.

In FIGS. 9A and 9B, electronic gas meter platform 802 comprises a processor 904, a storage device 906 as well as user interface 818. Processor 904 is coupled to storage device 906 and user interface 818. Electronic gas meter platform 802 (e.g. processor 904) may also be coupled to other sensors or components. As shown, processor 904 is coupled to magnetic metering unit 813 for other measurements such as revolution counter data to determine a flow rate.

Electronic gas meter platform 802 may further comprise wired communication interface 820 which is coupled electronically to processor 904.

Each of the user interface 818 and the wired communication interface 820 may provide a data communication interface, which may be an alarm signaling interface, controllable by processor 904 to communicate various data determined by processor 904, whether remotely and/or locally relative to meter 800. The data may comprise measured and/or calculated data and may comprise data that signals an alarm. Measured and/or calculated data may be pressure or differential pressure values, flow rates, etc. Alarm data may comprise a single indicating an alarm condition is detected, such as when a measured and/or calculated data value is out of a desired scope or range for such data value, where such scope or range may be defined by one or more thresholds. It may be preferred that processor 904 only stores and/or reports data such as to a remote device coupled thereto (not shown), which remote device then performs an alarm determination process, if desired.

It will be understood that processor 904 may provide pressure sensor signals and/or alarm signals as input data 408B to main control unit 404, which main control unit may process such data and/or relay alarm signals similarly as described in respect of vibration data and leak detection and gas blend detection. Processing aspects described for processor 904 whereby pressure data from sensors is processed, comparing to baselines and thresholds, etc. may be configured into main control unit 404.

An on-board (relative to platform 802) wireless communication interface (not shown) is another example of a data communication interface and it may be electronically controlled by processor 904.

Processor 904 may be a microprocessor, a microcontroller or other. Processor 904 may be implemented as a processor core, central processing unit (CPU) or other.

Storage device 906 may comprise a memory such as a programmable memory, for example, an electrically erasable read-only memory (EEPROM).

User interface 818 may be any one or more of a display screen, a light, a bell or other output device that may signal an alarm. It may be preferred to display the differential pressure value and/or alarm.

Electronic gas meter platform 802 may also comprise a wired communication interface 120, as noted, such as for communicating data including differential pressure data, flow rate data, corrective data, and/or alarm data. Wired communication interface 820 may be a component of the electronic gas meter platform. Wired communication interface 820 may be coupled to a short range and/or long range communication device (not shown) providing an external communication device. Short range and/or long range communication device may comprise an antenna and associated circuits. In an example, not shown, either short range or long range communication device may be on-board and internal to the rotary meter 800. A short range and/or long range communication device may be configured to communicate using known protocols or standards such as to communicate short message service (SMS) messages/text messages via a cellular network, messages via a Bluetooth™ network or Zigbee™ network, etc. (Bluetooth is a trademark of Bluetooth SIG, Inc. Zigbee is a trademark of Zigbee Alliance). Such messages may be alarm messages or data reporting messages or both. Wired communication interface may comprise a universal serial bus (USB), RS-232, Ethernet or other standard interface or a proprietary interface. Wired communication interface 820 may also provide access to storage device 906 such as for providing programming, to retrieve stored values, etc. However other interfaces or means to program storage device 906 may be provided.

Revolution counter data, (differential) pressure measurement data, as well as various parameters used to determine flow rate measurements from the sensor data as well as the determined flow rate data is stored to storage device 906 (e.g. EEPROM memory). One condition that may be monitored is flow rate. Flow rate monitoring is further described in U.S. Patent Application No. 62/981,791 filed Feb. 26, 2020 by the present applicant and is incorporated herein by reference in its entirety. For example, a working condition monitoring system for a positive displacement rotary flow meter determines flow rate and differential pressure information for logging to determine a history of such data for a meter in the field. Deviation from good working data established for the meter model may be used such as to indicate maintenance and/or repair needs. Mechanical or other wear in a meter may lead to higher differential pressure measures for a given flow rate (or a lower measured flow rate for a given differential pressure) than is true for a meter in good working order. A corrective factor responsive at least to a current different pressure may be applied to correct a measure of flow rate that is determined in response to a measure of impeller rotation to account for additional flow of gas through the meter that is not driving the impeller(s).

In an embodiment, the system comprises a main control unit coupled to each of: a first pressure communication assembly and a second pressure communication assembly to provide pressure information from separate first and second locations within a positive displacement rotary meter to be monitored; a magnetic metering unit providing rotation information for the meter, the rotation information useful to determine flow rates; at least one interface; and a storage device. The main control unit is configured to: determine a current differential pressure from the pressure information; determine a current flow rate from the rotation information; and store the current differential pressure in accordance with the current flow rate in interval records maintained by the main control unit. In an embodiment, the main control unit is configured to define each interval of the interval records in response to respective percentages of a maximum flow rate of the rotary meter, and use the current flow rate to determine which of the interval records to store the current differential pressure. In an embodiment, the storage device stores good working condition data defining a curve Q representing a baseline of differential pressure and flow rate data; and the main control unit is configured to: use the curve Q to determine a minimum allowable flow rate that is responsive to the current differential pressure; and, at least one of log to the storage device and communicate via the at least one interface an alarm if the current flow rate is lower than the minimum allowable flow rate.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

In accordance with an embodiment, there is provided a meter set monitoring system comprising: at least one sensing unit each positioned at a respective location of a meter set to be monitored to provide at least one sensing unit signal; and a control unit configured to be coupled to the at least one sensing unit and further to one or more alarm signaling units. The control unit is configured to: detect a condition from the respective location using the at least one sensing unit signal; and communicate to at least one of the one or more alarm signaling units to provide an alarm signal in response to the condition.

In an embodiment, the at least one sensing unit comprises at least one sensor and at least one processor. In an embodiment, the at least one sensing unit senses any one of flow rate, fluid levels, differential pressure, oil condition and vibration. In an embodiment, the condition corresponds to an abnormality at the at least one location.

In an embodiment, detecting a condition comprises comparing a respective sensing unit signal from a respective sensing unit to a stored baseline for the respective sensing unit.

In an embodiment, the stored baseline for the respective sensing unit is determined by measuring a respective sensing unit signal during a normal operation of the meter set. In an embodiment, the control unit is configured to receive the respective sensing unit signal during the normal operation and define the stored baseline.

In an embodiment, the alarm signal is provided by comparing the at least one sensing unit signal to a stored abnormal sensing unit signal. In an embodiment, the stored abnormal sensing unit signal is determined by measuring a sensing unit signal at the at least one location during abnormal operation.

In an embodiment, the one or more alarm signaling units are located in a remote location relative to the at least one sensing unit.

In an embodiment, the one or more alarm signaling units comprise a dashboard interface to present the alarm signal.

In an embodiment, the condition at the at least one location is any one of: a fluid leak in the meter set; a failure of at least one component of the meter set; a vandalism of the meter set; an unauthorized use of the meter set; a tampering of the meter set; and a change in gas blend. In an embodiment, the at least one sensor unit comprises a vibration sensor unit providing a vibration signal and the condition is determined using the vibration signal.

In an embodiment, the at least one sensing unit signal is an indicator of a fluid leak in proximity to the at least one location. In an embodiment, the condition corresponds to a fluid leak in proximity to the at least one location. In an embodiment, the alarm signal alerts of a fluid leak located in proximity to the at least one location.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

The invention claimed is:

1. A gas meter set monitoring system comprising:
a vibration sensing unit configured to be positioned at a respective location to monitor a meter set and to provide a vibration sensing unit signal; and
a control unit configured to be coupled to the vibration sensing unit and further to one or more alarm signaling units;
wherein the control unit is configured to:
detect a first condition of vibration comprising a change in gas blend or gas density from the location using the vibration sensing unit signal; and
communicate to at least one of the one or more alarm signaling units to provide an alarm signal in response to the first condition of vibration.

2. The system of claim 1, wherein the vibration sensing unit comprises at least one vibration sensor, at least one processor and a communication component to communicate the vibration sensing unit signal.

3. The system of claim 1, wherein the control unit is configured to detect a further condition of vibration corresponding to an abnormality at the location, wherein an abnormality comprises any one of:
a fluid leak in the meter set;
a failure of at least one component of the meter set;
a vandalism of the meter set;
an unauthorized use of the meter set; and
a tampering of the meter set.

4. The system of claim 1, wherein the condition of vibration corresponds to a determination of a gas blend or a gas density at the at least one location.

5. The system of claim 1, wherein detecting the further condition of vibration comprises comparing the vibration sensing unit signal unit to a stored baseline for the vibration sensing unit, using a current gas blend or gas density to select the stored baseline for comparing to the vibration sensing unit signal.

6. The system of claim 5, wherein the stored baseline for the vibration sensing unit comprises a signal representing one of: a normal operation of the meter set; and an abnormal operation of the meter set.

7. The system of claim 1, wherein the control unit is configured to detect the first condition of vibration using a classifier comprising any one of: a Logistic Regression, a Naive Bayes, a Perceptron, a Decision Tree, a Random Forest or a Kernel estimation type classifier; a Support Vector Machine, or an Artificial Neural Network.

8. The system of claim 1, wherein, during operation, the one or more alarm signaling units are located in a remote location relative to the vibration sensing unit.

9. The system of claim 1, wherein the control unit provides data to the one or more alarm signaling units for presentation via a dashboard interface to present the alarm signal.

10. The system of claim 1, wherein the alarm signal alerts of a fluid leak located in proximity to the at least one location.

11. The system of claim 1, wherein in respect of the meter set, the control unit is further configured to be coupled to one or more respective meter set sensors sensing a working condition of the meter set, each of the one or more respective meter set sensors being separate from the sensing unit and the one or more respective meter set sensors providing a working condition signal; and wherein the control unit is further configured to: detect a working condition of the meter set using the working condition signal; and communicate to at least one of the one or more alarm signaling units to provide an alarm signal in response to the working condition.

12. The system of claim 11, wherein the one or more respective meter set sensors comprise any of a pressure sensor and a sensor to measure oil condition.

13. The system of claim 1 further comprising a messaging middleware component to communicate between: the at least one vibration sensing unit and the control unit; and the control unit and the one or more alarm signalling units.

14. A computer implemented method comprising steps executed by a control unit configured to monitor a meter set:
receiving, at the control unit, a vibration sensing unit signal from a vibration sensing unit positioned at a location to monitor a meter set;
detecting, by the control unit, a first condition comprising a change in a gas blend or a gas density at the location using the at I act onc vibration sensing unit signal; and
communicating, by the control unit, to at least one of one or more alarm signaling units to provide an alarm signal in response to the first condition.

15. The method of claim 14, wherein:
the vibration sensing unit comprises a vibration sensor, a processor and a communication component to communicate the vibration sensing unit signal; and
the meter set comprises a gas meter set.

16. The method of claim 14, wherein the control unit is configured to detect a further condition corresponding to an abnormality at the at least one respective location, the abnormality comprising any one of:
a fluid leak in the meter set;
a failure of at least one component of the meter set;
a vandalism of the meter set;
an unauthorized use of the meter set; and
a tampering of the meter set.

17. The method of claim 14, wherein detecting the first condition comprises one of: comparing the vibration sensing unit signal to a stored baseline; and classifying using a classifier comprising any one of:
a Logistic Regression, a Naive Bayes, a Perceptron, a Decision Tree, a Random Forest or a Kernel estimation type classifier; a Support Vector Machine, or an Artificial Neural Network.

18. The method of claim 17, wherein detecting the first condition comprises the comparing of the vibration sensing unit signal to the stored baseline, wherein the comparing is responsive to a current gas blend, such that the stored baseline is selected in response to the current gas blend.

19. A gas meter set monitoring system comprising:
a vibration sensing unit configured to be positioned at a location of a meter set to be monitored, and to provide a vibration sensing unit signal; and
a control unit configured to be coupled to the vibration sensing unit and further to one or more alarm signaling units;
wherein the control unit is configured to:
detect a condition of vibration from the location using the vibration sensing unit signal; and
communicate to at least one of the one or more alarm signaling units to provide
an alarm signal in response to the condition of vibration;
wherein detecting the condition of vibration comprises comparing the vibration sensing unit signal to a stored baseline for the vibration sensing unit; and
wherein detecting the condition of vibration is responsive to the current gas blend to select the stored baseline.

20. A gas meter set monitoring system comprising:
a vibration sensing unit configured to be positioned at a location to monitor a meter set, and to provide a vibration sensing unit signal; and
a control unit configured to be coupled to the vibration sensing unit and further to one or more alarm signaling units;
wherein the control unit is configured to:
detect a first condition of vibration comprising a change in gas blend or gas density from the location using the vibration sensing unit signal; and
communicate to at least one of the one or more alarm signaling units to provide an alarm signal in response to the first condition of vibration; and
wherein the control unit is further configured to be coupled to one or more respective meter set sensors sensing a working condition of the meter set, each of the one or more respective meter set sensors being separate from the vibration sensing unit and the one or more respective meter set sensors providing a working condition signal; and
wherein the control unit is further configured to: detect a working condition of the meter set using the working condition signal; and communicate to at least one of the one or more alarm signaling units to provide an alarm signal in response to the working condition.

21. The system of claim 20, wherein the one or more respective meter set sensors comprise any of a pressure sensor and a sensor to measure oil condition.

* * * * *